United States Patent [19]

Wells, Jr.

[11] 4,001,283
[45] Jan. 4, 1977

[54] METHOD FOR THE MANUFACTURE OF FURFURAL USING HYDROGEN CHLORIDE

[76] Inventor: Preston A. Wells, Jr., 345 Locust Road, Winnetka, Ill. 60093

[22] Filed: Sept. 14, 1970

[21] Appl. No.: 71,831

Related U.S. Application Data

[63] Continuation-in-part of Ser. No. 761,734, Sept. 23, 1974, abandoned.

[52] U.S. Cl. .............................................. 260/347.9
[51] Int. Cl.$^2$ ...................................... C07D 307/50
[58] Field of Search .................................. 260/347.9

[56] References Cited

UNITED STATES PATENTS

| | | | |
|---|---|---|---|
| 1,919,877 | 7/1933 | Brownlee | 260/347.9 |
| 2,689,250 | 9/1954 | Natta | 260/347.9 |
| 2,818,413 | 12/1957 | Natta | 260/347.9 |
| 3,199,958 | 8/1965 | Skugh | 260/347.9 |

OTHER PUBLICATIONS

Handbook of Chemistry and Physics, 43rd. Edition, 1961–1962, The Chemical Rubber Publishing Co., Cleveland, Ohio, p. 582.

*Primary Examiner*—Henry R. Jiles
*Assistant Examiner*—Bernard Dentz
*Attorney, Agent, or Firm*—Fitch, Even, Tabin & Luedeka

[57] ABSTRACT

A method for producing furfural from pentosan-containing materials wherein steam and a volatile acid catalyst are introduced into a bed of the pentosan-containing material, the moisture content of which is minimized.

5 Claims, 3 Drawing Figures

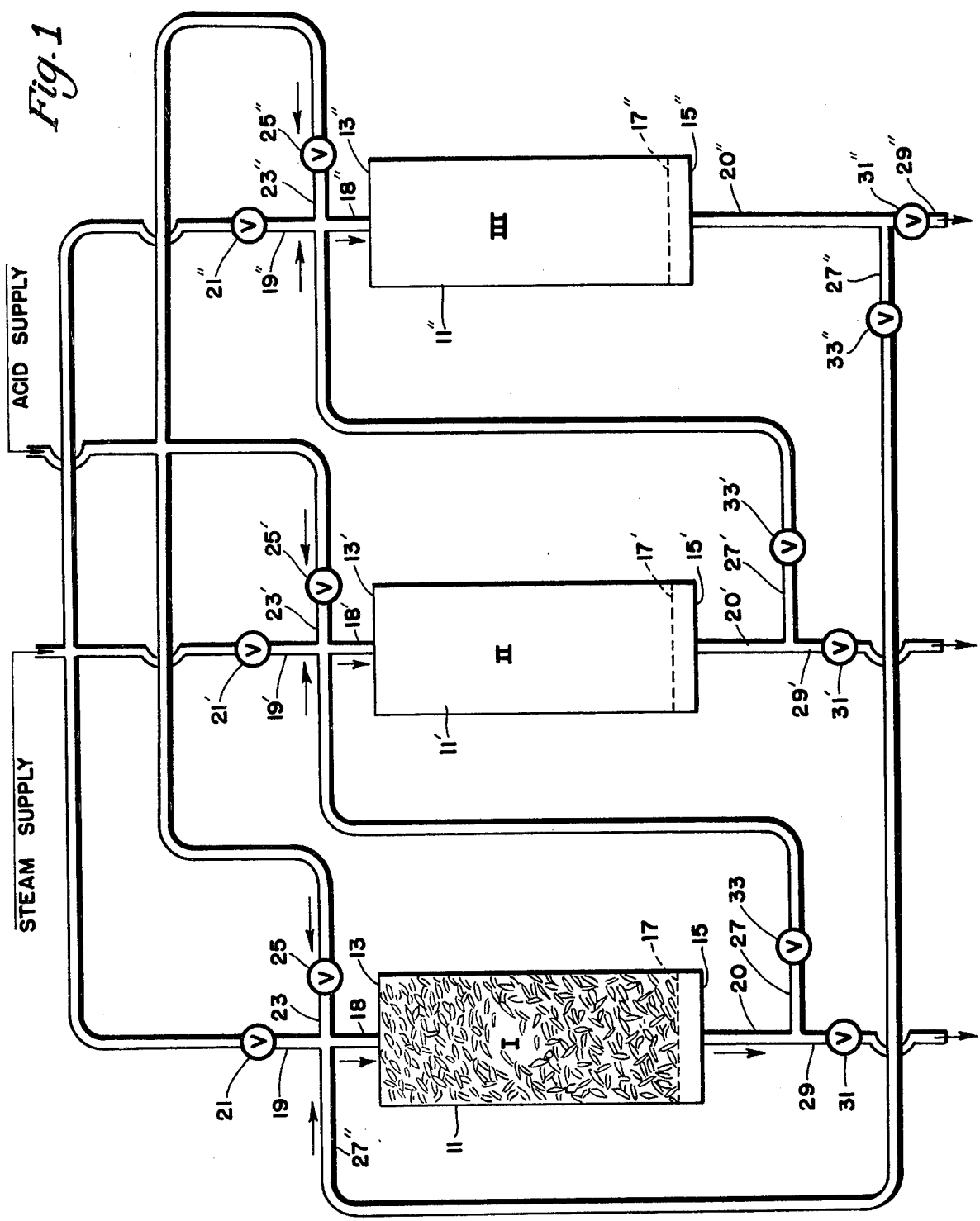

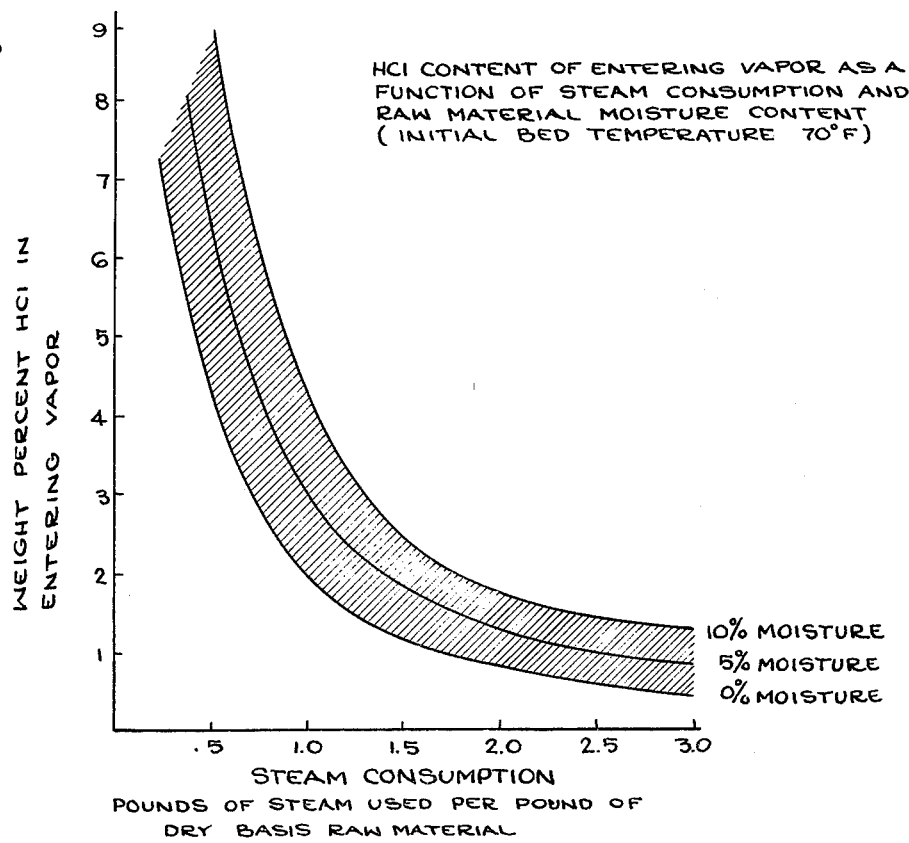
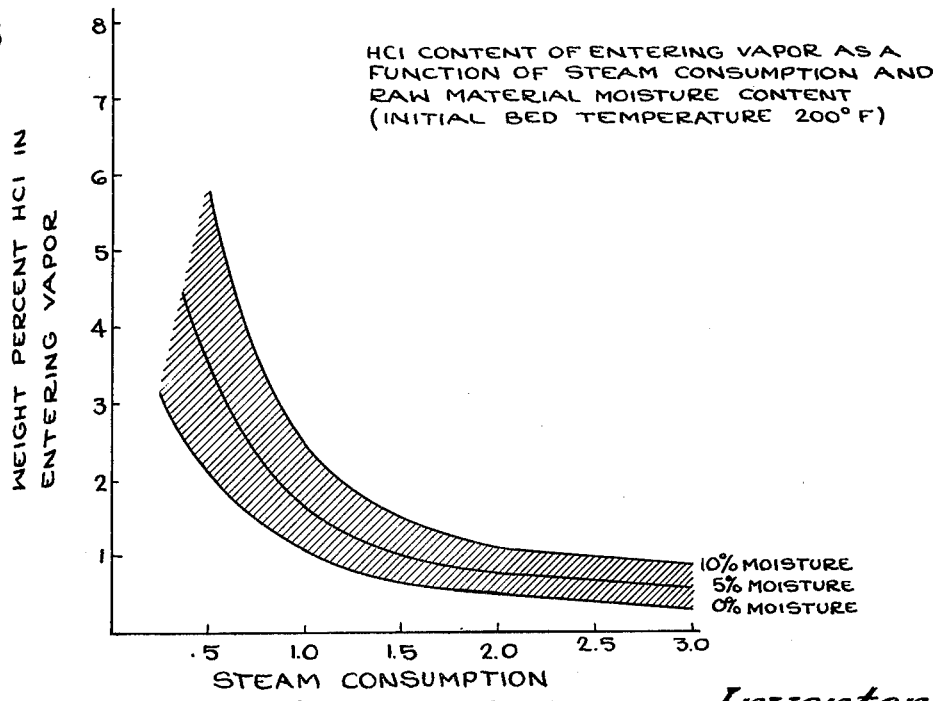

METHOD FOR THE MANUFACTURE OF FURFURAL USING HYDROGEN CHLORIDE

This application includes subject matter disclosed in my co-pending application Ser. No. 761,734, filed Sept. 23, 1968 now abandoned.

This invention relates generally to the manufacture of furfural, and it particularly relates to the preparation of furfural by treatment of pentosan-containing material in the presence of water and a volatile acid catalyst.

For many years, furfural has been made commercially from pentosan-containing organic materials such as oat hulls, rice hulls, cottonseed hulls, flax shives, corn hulls, olive waste, peanut hulls, sunflower seed hulls, corn cobs, bagasse and other similar materials. Under the proper conditions, the pentosans in such materials undergo reaction in the presence of water to provide furfural. Side reactions also take place to produce other products, but the desired furfural reaction is illustrated by the following generalized reaction:

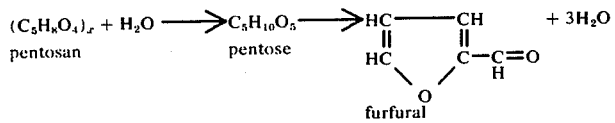

Commercially, the reaction has been carried out by conducting steam into a dampened bed of the pentosan-containing material. The steam serves to heat the bed to a temperature at which the desired hydrolysis reaction between the pentosans and water will take place at a satisfactorily rapid rate. The water which takes part in the reaction is thus provided by the moisture present in the dampened bed and the condensate obtained from the steam in heating the bed to operating temperature. The steam further serves to steam-distill the furfural reaction product from the bed, so that a vapor mixture of steam, furfural, and by-products is produced, which vapor mixture is subsequently condensed and further processed to recover the desired furfural product.

It is also known that the reaction rate between water and the pentosan-containing material can be increased by the provision of certain catalysts. Various acids act as catalysts, examples being sulfuric acid, phosphoric acid and hydrochloric acid. Practically all of the present commercial furfural processes use sulfuric acid as the catalyst, with perhaps a few using phosphoric acid. To the best of applicant's knowledge hydrochloric acid is not utilized as a catalyst in any existing commercial operations. One of the reason why hydrochloric acid has not been used is that it is a relatively volatile acid, and at the temperatures and concentrations of acid at which the furfural reaction proceeds satisfactorily, the vapor pressure of the hydrogen chloride in the liquid hydrochloric acid is relatively high. This, it has heretofore been believed, inherently resulted in excessive loss of acid from the bed unless a substantial amount of liquid water was also added.

Sulfuric acid, on the other hand, is substantially non-volatile and has been the catalyst of choice. However, because of its non-volatility and in order to properly contact the pentosan-containing material with sulfuric acid, the acid must be placed in dilute aqueous solution and spread or stirred into the pentosan-containing material. If it is made sufficiently dilute to readily wet all of the material, the water of dilution has an adverse effect on efficiency. Moreover, stirring to effect contact of the pentosan-containing material with the sulfuric acid requires massive equipment, which increases costs.

It is also known that the reaction rate between water the the pentosan-containing material can be increased by operating at elevated temperatures. Inasmuch as water is one of the reactants, it is not possible to operate at temperatures substantially greater than 100° C. unless the reaction is carried out at elevated pressure. This requires the use of pressure vessels, which increases the capital investment.

Attempts have also been made to improve the reaction rate by utilizing high concentrations of acid in the reaction system. However, the use of additional acid entails additional cost, either in increased consumption of acid or in increased capital investment and operating cost connected with an acid recovery system.

It is, therefore, the general object of the present invention to provide a method for the manufacture of furfural from pentosan-containing materials in which a volatile acid is utilized as a catalyst and whereby one or more of the foregoing disadvantages are overcome. A more specific object of the present invention is to provide such a method wherein the volatile acid utilized as a catalyst comprises hydrochloric acid or hydrogen chloride. This and other objects of the invention will become apparent from the following description and from the drawing in which:

FIG. 1 is a flow sheet chosen to illustrate the principals of the present invention;

FIG. 2 is a graph showing the relationship between the HC1 content of the vapor entering the bed and the steam flow rate into the bed for three raw material moisture contents of zero, five, and ten percent moisture, respectively, with an initial bed temperature of 70° F; and FIG. 3 is a graph like that of FIG. 2 except based on an initial bed temperature of 200° F.

Generally, in accordance with the present invention, there is provided a process for the manufacture of furfural which can be performed at substantially atmospheric pressure in uncomplicated and inexpensive processing equipment. The process provides acceptably low acid catalyst consumption without the necessity for auxiliary catalyst recovery systems.

More particularly, and with reference to the drawing, there is provided a reactor system I in which the pentosan-containing material is contacted with steam and a volatile acid catalyst. Additional reactor systems II and III are also illustrated in the drawing which are essentially identical to reactor system I. In another embodiment of the present invention reactor systems II and III are utilized in conjunction with reactor system I to provide optimum reaction efficiency, as will subsequently be described. For the present, however, the flow chart for reactor system I will be separately described.

The reactor system I preferably comprises a cylindrical vessel 11 having a vertical axis. It is closed at the top and bottom by heads 13 and 15, respectively. The vessel 11 is constructed of material which is resistant to corrosion by the materials contained therein, and in the preferred embodiment wherein hydrochloric acid is used as the volatile acid catalyst, the vessel 11 may be constructed of glass, ceramic or plastic lined vessels.

The vessel 11 is initially charged with the pentosan-containing material, such as rice hulls, corn cobs, etc., through a suitable port (not illustrated) in the top head 13. A grid 17 is provided in the vessel 11 adjacent the bottom which supports the pentosan-containing material above the bottom head 15, but which permits the passage of vapor downwardly therethrough.

An inlet connection 18 is provided in the top head 13 through which vapor comprising steam and volatile acid are introduced into the vessel 11, in the direction indicated by the arrow. An outlet connection 20 is provided in the bottom head 15 through which vapor comprising steam, reaction products, and (in later stages of reaction of the bed) volatile acid catalyst are removed from the vessel 11, in the direction indicated by the arrow. This results in a generally downward flow of vapor through the bed of pentosan-containing material in the vessel 11, but it should be understood that this direction of flow, while it is preferable in certain respects, is not necessary in order to enjoy the benefits of the invention, and flow of vapor upwardly through the bed is also possible and contemplated herein.

Steam may be introduced into the vessel 11 through the inlet connection 18 from a steam line or conduit 19, and the rate of introduction is controllable by a suitable valve 21. Volatile acid catalyst may be introduced into the vessel 11 through the inlet connection 18 from an acid line or conduit 23, and the rate of introduction of acid is controllable by a suitable valve 25. Another supply line or conduit 27'' is also provided which is in communication with the inlet connection 18, the purpose of which will be subsequently explained in connection with the embodiment of the invention in which all three reactor systems are utilized.

The outlet connection 20, through which vapor is discharged from the vessel 11, is in communication with two lines or conduits 29 and 27, and vapor discharged from the vessel 11 may be directed into one or the other of these lines by opening or closing valves 31 and 33. In further description of reactor system I, it will be assumed that valve 33 is closed and valve 31 is opened, so that vapor is discharged from the vessel 11 through line 29, as indicated by the arrow.

As previously indicated, the vessel 11 is charged with raw material comprising a pentosan-containing material to provide a bed through which vapor is capable of passing. It is an important feature of this invention that the raw material is not dampened or wetted with water in the liquid phase, but instead that the moisture content of the pentosan-containing material in the bed is no greater than the natural moisture content. By "natural moisture content" is meant the normal moisture content of the commercially-available material; for example in the case of rice hulls the natural moisture content is between about 5 and 9 percent by total weight of rice hulls. In a preferred embodiment of the present invention the moisture content of the raw material which is used to make up the bed contains no more than ten percent moisture by weight and, within practicable limitations, contains substantially less than ten percent moisture, i.e., from zero moisture content up to 10 percent moisture by weight.

Moreover, increase in moisture content of the pentosan-containing material in the bed is minimized following formation of the bed and during reaction. The provision of a minimal moisture content in the bed before and during reaction provides unexpected results, as will be more particularly pointed out hereinafter, and is one of the ways in which the present invention is distinguishable from the prior art.

In this connection, it has heretofore been believed that in order to retain a volatile acid catalyst in the reaction system during the manufacture of furfural it was essential to introduce liquid water into the pentosan-containing material so as to bring its moisture content substantially above its natural moisture content. For example, U.S. Pat. No. 2,818,413 specifically teaches that in order to eliminate the loss of volatile acid catalyst during the reaction it is necessary to introduce water in such large amounts as to strip all of the volatile acid from the system, and that the amount of water required to accomplish this purpose is about 20 to 30 percent by weight of dry pentosan-containing material. This and other prior art patents consistently teach the desirability and necessity of adding water in the liquid phase to the pentosan-containing material. Frequently, as in U.S. Pat. No. 1,919,877, the patents refer to "dampening" the pentosan-containing material. "Dampening" is often not defined, but from the examples in the patents and from general usage of that term in the art it refers to the addition of at least about 25 percent water by weight of the original pentosan-containing material. In all of the prior art of which applicant is aware, the moisture content of the raw material making up the bed initially has been at least 15 percent by weight, and usually much higher, prior to introduction of steam into the bed.

In accordance with the teachings of the present invention, in which the moisture content of the bed is minimized at all times, not only has it been found possible to retain the volatile acid catalyst in the bed for most of the reaction period, but there also results an economy in the amount of volatile acid employed. It is believed that the optimum conversion of pentosans into furfural occurs when the concentration of volatile acid catalyst in the liquid aqueous phase in the pentosan-containing material is in the range of 10 to 16 percent. By minimizing the level of water in the liquid phase as disclosed herein it is possible to operate in this optimum acid range with minimum amounts of acid. This is in distinct contrast to the amount of volatile acid which would be required to obtain optimum concentrations if the bed were dampened with water, as previously thought necessary. By the same token, the amount of volatile acid remaining in the bed after reaction is minimized by the present invention.

In operation of the reactor system I, after establishment of the bed of pentosan-containing material, steam and volatile acid are concurrently introduced into the inlet connection 18 of vessel 11 through lines 19 and 23, respectively. As previously indicated, the reaction proceeds at a satisfactory rate at atmospheric pressure, so that saturated steam at a temperature of about 100° C. may be utilized. It should, however, be understood that superheated steam may also be used if desired, although an excessive amount of superheat will result in undesired charring of the pentosan-containing material of the bed, and produces undesirable by-products.

Preferably, if superheated steam is used it should have no more than 40°–50° C. of superheat. Saturated steam at greater than atmospheric pressure may also be utilized although, as previously indicated, this requires more expensive pressure equipment which generally is to be avoided.

The volatile acid which is used is preferably hydrogen chloride, and it is added at a level selected to provide optimum operating efficiency. A high level of acid will result in more rapid propagation of the reaction through the bed, but will also result in a lowe yield of furfural. A low acid level will result in slower propagation of the reaction through the bed and in higher yield of furfural, but it also requires the addition of more steam which increases costs. The relationship between the HCl content in the entering vapor and steam consumption for raw material having initial moisture contents between zero and ten percent is depicted in the graph of FIG. 2. The graph of FIG. 2 is based on an initial bed temperature, before introduction of steam, of 70° F.

It will be apparent that beginning with a bed which is at ambient temperature there will be condensation of steam in the bed as a consequence of raising the temperature of the bed to operating temperature. This inherently results in an increase in the overall water content of the pentosan-containing material. The amount of water thus introduced is not large because of the relatively low specific heat of the pentosan-containing material as compared with the high heat of condensation of steam. It does nevertheless result in higher acid consumption, and the graph of FIG. 3 illustrates the decreased acid consumption enjoyed when the initial bed temperature, before introduction of steam is 200° F instead of 70° F. For example, when utilizing one pound of steam per pound of raw material and a bed comprising 10 percent moisture, the required concentration of acid in the entering vapor is about 4.4 percent when the initial bed temperature is 70° F (FIG. 2). On the other hand, when the initial bed temperature of 200° F and the other variables remaining the same, the required concentration of acid in the entering vapor is about 2.5 percent (FIG. 3). Thus, it is advantageous to have the bed at elevated temperature prior to introduction of steam and although heating with steam is efficient it may nevertheless be desirable under some circumstances to preheat the bed by other means. It has been found suprisingly and unexpectedly that not only is it not necessary to add water to the raw material in order to retain the volatile acid catalyst in the bed during the reaction, it is also possible to lower the moisture content of the raw material to less than its natural moisture content without adverse effect and, in fact, thereby obtain even greater economy of volatile acid catalyst. Of course, drying of the raw material also involves increased expense and may not be economic in some cases, but the fact that volatile acid catalyst, particularly hydrochloric acid, can be retained in the bed even when the moisture content of the bed approaches zero is contrary to the prior art practice.

It is readily apparent from FIGS. 2 and 3 that the process of the present inventon provides substantially improved economy of volatile acid catalyst in comparison with prior art processes involving raw material having a moisture content of 15 percent or more.

In accordance wih the present invention, reaction of the pentosan-containing materials with water is carried out utilizing a static bed, and in one embodiment of the present invention the reaction begins adjacent the top of the bed as operating conditions of temperature and acid level are achieved. As previously indicated, desirable operating conditions are about 100° C. and between about 10 and 16 percent hydrochloric acid by weight in the liquid phase, and preferably about 12 percent hydrochloric acid by weight in the liquid phase. It is believed that at these conditions the reactions producing furfural proceed to substantial completion in about 4 hours. During the 4 hour reaction period, steam should be continuously introduced so as to steam-distill off the furfural as it is formed to thereby minimize undesired reaction between furfural and other compounds present in the bed.

Beginning at the top of the bed, reaction between the water and the pentosan-containing materials proceeds in a zone which moves progressively dowwardly through the bed. As previously pointed out, the rate at which the reaction zone moves downwardly is functionally related to the rate at which steam and volatile acid are introduced into the vessel.

Ordinarily, in order to achieve maximum volumetric efficiency of reactor system I the rate of steam flow will be held constant at a maximum economic rate. Therefore, for practical purposes the rate of propagation of the reaction zone is determined by the rate of addition of the volatile acid catalyst.

The pentosan-containing material at the top of the bed will be maintained at reaction conditions for substantially more than four hours, whereas material at the bottom of the bed should be maintained at reaction conditions for only slightly more than 4 hours.

Under the operating conditions hereinabove described, shortly after the pentosan-containing material at the top of the bed attains reaction conditions, furfural vapors begin to appear in admixture with the exit gases from outlet connection 20 of the vessel 11. The concentration of furfural in the outlet gases gradually increases until it attains a maximum concentration which is functionally related to the ratio of steam to volatile acid being introduced into the vessel, and to the type of pentosan-containing material in the bed. In any event, there is substantially no volatile acid catalyst in the mixture of gases leaving the vessel 11 for a substantial part of the reaction period, until the reaction zone has progressed downwardly throughout most of the bed. Thus, the volatile acid catalyst is retained in the reactor system I throughout most of the reaction. This is contrary to the teachings of the prior art in that it is not necessary to add liquid water to the bed to achieve this end.

EXAMPLE I

As an example of the embodiment of the invention thus far described, rice hulls were utilized as the pentosan-containing material. The rice hulls contained approximately 5.7 percent moisture, which is the natural moisture content of rice hulls as commercially available. Saturated steam at substantially atmospheric pressure was introduced into the top of the bed of rice hulls, together with gaseous hydrogen chloride. The steam was introduced at a rate of 0.2 parts of steam per part of rice hulls per hour. The hydrogen chloride was introduced at a level to provide 1.9 parts of hydrogen chloride per 100 parts of steam. Shortly after the introduction of steam and hydrogen chloride was begun, furfural vapors appeared in the exit gases from the bottom of the bed. The furfural concentration in the exit gases gradually increased to a maximum of about 5.3 percent, and subsequently gradually decreased after the front of the reaction zone reached the bottom of the bed. The introduction of steam and hydrogen chloride was continued for about 11 hours, and for about the first 6 hours there was substantially no hydrogen chloride in the gases exiting from the reaction. This showed that it is not necessary to add water to the bed in order to maintain the hydrogen chloride in the bed for the length of time required for commercial production of furfural, as heretofore believed necessary.

At the end of 11 hours, a total of 0.07 parts of furfural were obtained per part of rice hulls, or a yield of 7 percent based on the weight of rice hulls. The total usage of steam was 2.2 parts of steam per part of rice hulls. The total hydrogen chloride feed was 0.042 parts per part of rice hulls. 0.020 parts of hydrogen chloride per part of rice hulls were retained in the bed residue.

It should be pointed out that because the process of Example I was a batch process instead of a continuous process, steady state conditions were not achieved. Consequently, it is not possible to directly relate all of the interrelationships depicted in FIGS. 2 and 3 with Example I. This will be done in connection with the continuous process next to be described.

Next considering the further embodiment depicted in the drawing by the combination of reactor systems I, II, and III, it will be seen that each of reactor systems II and III have elements which correspond to the elements previously described in connection with reactor system I. These elements are identified by the same numerals used in connection with reactor system I, but are further designated by the symbols "prime" (') and "double prime" (") for reactor systems II and III, respectively.

Reactor systems I, II, and III are interconnected by lines or conduits 27, 27', and 27". Line 27 connects the outlet connection 20 of reactor system I with the inlet connection 18' of reactor system II; Line 27' connects the outlet connection 20' of reactor system II with the inlet connection 18" of reactor system III; and the line 27" connects the outlet connection 20" of reactor system III with the inlet connection 18 of reactor system I. These lines permit serial operation of the reactors to provide substantially improved efficiency and economy of steam and volatile acid, in the manner hereinafter described.

Each of the reactor systems I, II, and III is initially charged with pentosan-containing material having its natural moisture content to provide a bed, as previously described. Operation is begun by introducing steam and volatile acid into the vessel 11 of reactor system I, also as previously described. After the introduction of steam and volatile acid catalyst is begun, furfural begins to appear in the exit gases in the outlet connection 20, without, however, any volatile acid catalyst being present in the exit gases. This stage of this embodiment of the process of the present invention will be hereinafter referred to as stage A. Throughout stage A, the mixture of gases leaving reactor system I is conducted through line 29 to storage or to further processing to enable recovery of furfural therefrom.

As the reaction proceeds progressively dowwardly through the bed in reactor system I, it eventually reaches a point at which volatile acid catalyst begins to appear in the exit gases. At the time that volatile acid catalyst appears in the exit gases, valve 31 is closed and valve 33 is opened so that the exit gases from reactor system I are conducted into line 27 and thence into the inlet connection 18' of reactor system II. The exit gases at this point comprise steam, volatile acid catalyst, furfural, and by-products. The introduction of this gaseous mixture into reactor system II results in initiation of reaction in reactor system II, in the same manner previously described in connection with reactor system I. Shortly after introduction of gases into reactor system II is initiated, gases begin exiting from the outlet connection 20 of reactor system II, which exit gases include furfural, but do not include volatile acid catalyst. This stage of the process of this embodiment will hereinafter be referred to as stage B.

Obviously, stage B could be initiated some length of time after the volatile acid catalyst begins to appear in the exit gases from reactor system I. However, it is of advantage to utilize the volatile acid catalyst to the greatest possible extent by transferring as soon as possible. The transfer to reactor system II desirably should be made at least by the time the concentration of volatile acid catalyst in the exit gases reaches half that in the mixture being added to reactor system I.

Some time after the beginning of stage B, when the exit gases from reactor system I first include volatile acid catalyst, the furfural content of the exit gases from reactor I begins to decrease, which is the preferred time for the initiation of stage C. Stage C is initiated by closing valve 25 and thereby terminating the introduction of volatile acid into reactor system I, and opening valve 25', thereby beginning introduction of volatile acid catalyst into reactor II through line 23'. The rate of addition of volatile acid catalyst into reactor system II through line 23' is controlled so that the total amount of volatile acid catalyst introduced through both line 27 and 23' provides the desired level of volatile acid catalyst in the inlet connection 18'.

Throughout stages B and C of the process, the exit gases from reactor system II are conducted through line 29' for storage or for recovery of furfural, there being no volatile acid catalyst in the exit gases from reactor system II. During stage C, steam continues to be introduced into reactor I through line 19, and serves to strip the bed in reactor system I of as much volatile acid catalyst as possible. This mode of introduction of steam is continued until optimum recovery of volatile acid catalyst is achieved, but preferably is terminated no later than the beginning of stage E, hereinafter described.

Stage D begins when volatile acid catalyst first appears in the exit gases from reactor system II. At this point, valve 31' is closed and valve 33' is opened, so that the exit gases from reactor system II are conducted into line 27' and thence into reactor system III through its inlet connection 18".

Shortly after the beginning of stage D, exit gases including furfural but not including volatile acid catalyst appear from reactor system III. Throughout stage D these exit gases are conducted through line 29" for recovery of furfural, in like manner to that described in connection with reactor systems I and II. Similarly, at about the time that the furfural content in the exit gases from reactor system II begins to decrease, introduction of volatile acid catalyst into reactor system II is terminated, and introduction of volatile acid catalyst into reaction system III through line 23" is begun. This marks the beginning of stage E. As previously indicated, it is preferred that no later than at this time steam introduction into reactor system I be terminated by closing valve 21. Valve 21' is opened so that direct introduction of steam into reactor system II through line 19' is initiated. At least by this time, reactor system I has been isolated from the remainder of the system, its bed of pentosan-containing material having been exhausted of furfural and also exhausted of volatile acid catalyst to an optimum extent. Reactor system I is then ready for "turnaround" by discharging the exhausted bed therefrom and recharging the vessel 11 with fresh pentosan-containing material.

Stage F begins when volatile acid catalyst first appears in the exit gases from reactor system III, at which time valve 31" is closed and valve 33" is opened, thereby directing the exit gases into line 27" and thence into reactor system I. At this point, reactor system I has been "turned around" so that it is in condition for another cycle.

The same sequence is followed thereafter as has already been described for stages A through F. It will be seen that this embodiment of the process of the present invention permits greatly improved economy of materials. The furfural-containing gases which are discharged from the processes through lines 29, 29', and 29" contain little or no volatile acid, thereby minimizing corrosion problems in the furfural recovery system. Furthermore, the exhausted bed of pentosan-containing material is more comletely stripped of volatile acid catalyst, and the stripped volatile acid catalyst is utilized as a catalyst in the next reactor. An important result of this embodiment is that all of the volatile acid catalyst is usefully employed or recovered except that which remains in the exhausted bed.

EXAMPLE II

As an example of the embodiment of the present invention just described, three reactors were charged with rice hulls having a natural moisture content of 5.7 percent by weight, and at an initial temperature of about 70° F. A mixture of steam and hydrogen chloride was introduced into the first reactor system, with the hydrogen chloride being present at a level of 1.9 parts per 100 parts of steam. The steam was introduced at a rate of 0.2 parts of steam per part of rice hulls per hour. The furfural content in the exit gases from the first reactor system gradually increased to 5.3 percent by weight.

When hydrogen chloride first appeared in the exit gases from the first reactor system, the exit gases were shifted to the top of the second reactor system, and operation was continued at the same rates of introduction of steam and hydrogen chloride to the first reactor.

Operation was continued as previously described herein for stages A through F. After reaching steady state conditions, a yield of 0.064 parts of furfural per part of rice hulls was obtained, or 6.4 percent by weight of rice hulls. There were 0.012 parts of hydrogen chloride left in the exhausted bed per part of rice hulls. Thus, although the yield of furfural was very slightly lower than was obtained in Example I, the amount of hydrogen chloride retained in the exhausted rice hulls was substantially less than that which was retained in Example I. Moreover, the total steam usage was only about 1.5 parts per part of rice hulls, a substantial improvement over the 2.2 parts of Example I.

It should be pointed out that whereas it is known to use a series of reactors in the manufacture of furfural, as disclosed in U.S. Pat. No. 1,919,877, it has heretofore been taught that the bed should be dampened before the reaction is begun. Furthermore, in the patent just referred to, the bed is dampened throughout with hydrochloric acid before steam introduction is begun, which results in almost immediate production of hydrogen chloride in the exit gases. This, as previously indicated, is avoided in accordance with the present invention.

It is obvious that it is not necessary to use three reactors in series, and that four or more reactor systems may be used. Although two reactor systems theoretically would suffice, a certain amount of time is required to discharge the exhausted bed from a reactor system and charge the reactor system with fresh pentosan-containing material, and as a practical matter a minimum of three reactor systems are required. Obviously, the use of more than three reactor system entails additional capital cost.

Various modifications of the processes herein described will be apparent to those skilled in the art. Such modifications should be deemed to be within scope and spirit of the present invention.

Various of the features of the present invention are set forth in the following claims.

What is claimed is:

1. A method for producing furfural by reacting pentosan-containing material with water in the presence of hydrochloric acid catalyst, comprising the steps of establishing a static bed of the pentosan-containing material having a moisture content of less than 10 percent by weight and substantially free from hydrochloric acid catalyst, introducing steam and hydrogen chloride concurrently into the bed adjacent one end thereof, and recovering a furfural-containing mixture of gases at the other end of the bed, there being substantially no liquid water introduced into the bed before or during the course of the reaction.

2. The method of claim 1 in which the furfural-containing mixture of gases recovered from the bed is substantially free from hydrogen chloride during reaction of the majority of the pentosan-containing material in the bed.

3. The method of claim 1 in which steam and hydrogen chloride are introduced at preselected rates so as to provide operating conditions falling within the shaded areas of FIGS. 2 and 3.

4. A method for producing furfural by reacting pentosan-containing material with water in the presence of hydrochloric acid catalyst, comprising the steps of establishing a static bed of the pentosan-containing material in a first reaction zone and a static bed of the pentosan-containing material in a second reaction zone, said pentosan-containing material having a moisture content of less than 10 percent by weight and being substantially free from hydrochloric acid catalyst, introducing steam and hydrogen chloride concurrently into the bed of the first reaction zone adjacent one end thereof, recovering a furfural-containing mixture of gases at the other end of the bed during the period while said mixture is substantially free from hydrogen chloride, and conducting the furfural-containing mixture of gases from the first reaction zone into the second reaction zone when hydrogen chloride appears in said mixture, the furfural-containing mixture of gases from the first reaction zone being substantially free from hydrogen chloride during reaction of the majority of the pentosan-containing material in the bed of the first reaction zone, there being substantially no liquid water introduced into the beds before or during the course of the reaction.

5. The method of claim 4 in which steam and hydrogen chloride are introduced at preselected rates so as to provide operating conditions falling within the shaded areas of FIGS. 2 and 3.

* * * * *

UNITED STATES PATENT AND TRADEMARK OFFICE
CERTIFICATE OF CORRECTION

PATENT NO. : 4,001,283
DATED : January 4, 1977
INVENTOR(S) : Preston A. Wells, Jr.

It is certified that error appears in the above-identified patent and that said Letters Patent are hereby corrected as shown below:

Title page, code number 63, "September 23, 1974" should read ---September 23, 1968---.

Title page Column 2, line 1, "Skugh" should read ---Skogh---.

Column 2. line 7, "the" second occurrence should read --and--.

Column 2, line 43 "HCl" should terminate with an Arabic letter "l" instead of a numeral "1".

Column 5, line 11, "lowe" should be --lower--.

Column 5, line 16, "HCl" should terminate with an Arabic letter "l" instead of a numeral "1".

Column 5, line 62, "invention" is misspelled.

Signed and Sealed this

Twenty-ninth Day of March 1977

[SEAL]

Attest:

RUTH C. MASON
*Attesting Officer*

C. MARSHALL DANN
*Commissioner of Patents and Trademarks*